United States Patent
Jerebko et al.

(10) Patent No.: US 11,013,473 B2
(45) Date of Patent: May 25, 2021

(54) METHOD AND IMAGE RECONSTRUCTION DEVICE FOR VISUALIZING A REGION OF INTEREST, TOMOSYNTHESIS SYSTEM AND COMPUTER PROGRAM PRODUCT

(71) Applicant: SIEMENS HEALTHCARE GMBH, Erlangen (DE)

(72) Inventors: Anna Jerebko, Paoli, PA (US); Stefan Veitenhansl, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 85 days.

(21) Appl. No.: 15/933,652

(22) Filed: Mar. 23, 2018

(65) Prior Publication Data

US 2018/0271458 A1  Sep. 27, 2018

(30) Foreign Application Priority Data

Mar. 23, 2017 (EP) .................................. 17162573

(51) Int. Cl.

| | |
|---|---|
| *G06T 11/00* | (2006.01) |
| *A61B 6/02* | (2006.01) |
| *G06T 7/11* | (2017.01) |
| *A61B 6/00* | (2006.01) |
| *A61B 6/12* | (2006.01) |

(52) U.S. Cl.
CPC .............. *A61B 6/025* (2013.01); *A61B 6/502* (2013.01); *A61B 6/5205* (2013.01); *G06T 7/11* (2017.01); *G06T 11/003* (2013.01); *A61B 6/12* (2013.01); *G06T 2207/10016* (2013.01); *G06T 2207/10072* (2013.01)

(58) Field of Classification Search
CPC .... G06T 2211/436; A61B 6/025; A61B 6/463
See application file for complete search history.

(56) References Cited

U.S. PATENT DOCUMENTS

| | | | |
|---|---|---|---|
| 8,532,745 B2 | 9/2013 | DeFreitas et al. | |
| 9,047,498 B2 | 6/2015 | Dennerlein et al. | |
| 2014/0294138 A1 | 10/2014 | Jerebko | |
| 2014/0376691 A1* | 12/2014 | Hoernig ................ | G06T 11/006 378/37 |
| 2015/0036904 A1* | 2/2015 | Jerebko ................. | G06T 11/005 382/131 |
| 2015/0228092 A1* | 8/2015 | Claus .................... | G06T 11/006 382/131 |

(Continued)

FOREIGN PATENT DOCUMENTS

DE  102011087337 B4  10/2016

*Primary Examiner* — Kenneth J Malkowski
(74) *Attorney, Agent, or Firm* — Laurence Greenberg; Werner Stemer; Ralph Locher (57) ABSTRACT

A method for visualizing a region of interest inside an examination object into which an examination instrument has been introduced, and a tomosynthesis system for executing the method. Raw datasets are acquired from a number of lateral acquisition angles. A number of synthetic projections are calculated from the raw datasets. The synthetic projections are output in the form of an image sequence which represents the examination object in a rotating visualization. An image reconstruction device and a tomosynthesis system, as well as a computer program product and a computer-readable medium are described.

18 Claims, 2 Drawing Sheets

(56) References Cited

U.S. PATENT DOCUMENTS

| | | | |
|---|---|---|---|
| 2016/0071293 A1* | 3/2016 | Homann | G06T 11/008 378/21 |
| 2016/0089090 A1 | 3/2016 | Nakayama | |
| 2016/0235380 A1* | 8/2016 | Smith | A61B 6/025 |
| 2016/0256125 A1* | 9/2016 | Smith | A61B 6/025 |

* cited by examiner

METHOD AND IMAGE RECONSTRUCTION DEVICE FOR VISUALIZING A REGION OF INTEREST, TOMOSYNTHESIS SYSTEM AND COMPUTER PROGRAM PRODUCT

CROSS-REFERENCE TO RELATED APPLICATION

This application claims the benefit, under 35 U.S.C. § 119, of European patent application EP 17162573, filed Mar. 23, 2017; the prior application is herewith incorporated by reference in its entirety.

BACKGROUND OF THE INVENTION

Field of the Invention

The invention relates to a method for visualizing a region of interest, an image reconstruction device and a tomosynthesis system.

Many diagnostic methods exist to facilitate early detection of breast cancers. In addition to the traditional medical examination by palpation, two dimensional x-ray images are often produced in the form of projections of the breast, also known as mammograms. A problem with the latter approach is that, due to the overlapping of different tissue structures, pathological changes in the tissue are often hidden and therefore go undetected. In an attempt to compensate for this problem, images of the breast are acquired from two different angles, for example one projection in the craniocaudal (CC) direction, i.e. in the head-to-foot direction, and one projection at a 45° angle thereto (mediolateral oblique (MLO)).

The projection images, however, still provide no indication as to the malignancy or otherwise of the change. In other words, it remains unclear whether the change in the tissue is benign or malignant. In order to resolve this problem, it is generally necessary to take a tissue sample in the course of a biopsy, this being followed by a histological examination of the changes in the fine tissue structure. For the purpose of taking the sample, it is possible to localize the tissue change with the aid of the two stereotactic images that are acquired with compressed breast and stationary detector and with the x-ray source arranged at acquisition angles of +15° and −15° to a normal of the detection surface.

Another known method is the technique called tomosynthesis. The term describes an imaging method in which images of the breast are acquired from a plurality of different angles. To that end, projections are acquired with compressed breast within the scope of a tomosynthesis scan, for example with the x-ray source arranged at angles of 15 to 50 degrees to a normal of the stationary detection surface, the total dose being roughly equivalent to that of two conventional two-dimensional mammograms (that is to say e.g. CC and MLO). Typically, images for individual slices of the breast tissue are calculated, i.e. reconstructed, from the acquired projection data. The filtered backprojection method is frequently used in order to reconstruct a volume dataset of a region to be examined from the acquired projection data. The resulting volume dataset can be studied slice by slice for diagnostic purposes. Since slices above and below the slice selected for viewing in a particular case can be masked during the diagnostic assessment, pathological tissue changes are generally easier to recognize. In this case, however, the slices are represented from one direction only, so that, depending on the direction of the tissue change, it may still prove difficult to identify the change and to localize the same exactly.

During a subsequent biopsy by means of a biopsy needle, images are normally produced prior to or after a sample is actually taken in order to keep track of the position of the needle. Due to the needle introduced into the beam path, the acquisition of a complete tomosynthesis scan turns out to be difficult in this case, since interfering artifacts are caused in particular by large vacuum-assisted biopsy systems. For this reason, it is common practice to produce just two projections from fixed angles as control images in a purely stereotactic mode of operation. However, a good spatial impression of the position of the needle is difficult to obtain from these.

SUMMARY OF THE INVENTION

It is accordingly an object of the invention to provide a method for visualizing a region of interest which overcomes the above-mentioned and other disadvantages of the heretofore-known devices and methods of this general type and which provides for an improved spatial impression of a region of interest inside the examination object by means of a tomosynthesis system in spite of an examination instrument having been introduced into the examination object.

With the foregoing and other objects in view there is provided, in accordance with the invention, a method of visualizing a region of interest inside an examination object, the examination object having an examination instrument inserted therein. The novel method, which is performed by way of a tomosynthesis system, includes the following steps:

acquiring raw datasets from a plurality of lateral acquisition angles;

calculating a plurality of synthetic projections from the raw datasets; and outputting the synthetic projections in an image sequence that represents the examination object in a rotating visualization.

The method cited in the introduction for visualizing a region of interest within an examination object into which an examination instrument has been inserted is performed by means of a tomosynthesis system. The method comprises at least the following steps: In one step, raw datasets are acquired from a number of lateral acquisition angles. In a further step, a number of synthetic projections are calculated from the raw datasets. The synthetic projections are output in a further step in the form of an image sequence which represents the examination object in a rotating visualization.

The examination object can be an organ of a human or animal female patient, for example, though preferably the examination object will be a breast of a human female patient. In the following, therefore, the terms "examination object" and "breast of the patient" are used synonymously, without loss of generality. The region of interest concerns for example a micro calcification that is located inside the examination object, i.e. within the breast. Micro calcifications potentially indicate a carcinoma, since proliferating cells become necrotic over time and accumulate as calcium deposits. This region is represented or visualized with the aid of the method according to the invention in such a way that a good spatial position determination or localization is made possible. This is of advantage in particular in the case of a biopsy, because the positioning of the examination instrument, in other words e.g. of the biopsy needle, can be spatially accurately determined according to the invention and thereby visually checked, as will be explained in more detail later.

The raw data necessary for this preferably comprises a plurality of projection images, that is to say—in contrast to a stereotactic examination—preferably more than two. They can in principle be acquired by being retrieved e.g. from a storage device or via a network, though preferably they are acquired by means of a tomosynthesis device in the course of a preparatory step. To that end, the plurality of projection images of the examination object are produced by passing x-ray radiation through the examination object. For this purpose, the examination object is arranged between an x-ray source and a non-rotating detector. The x-ray source emits x-ray radiation, which is captured by the detector after a projection through the examination object. The x-ray source is in this case preferably adjustable over a defined angular range with respect to a central axis extending perpendicularly to the detector. The central axis can in this case extend in any direction in relation to the body of the patient. Preferably, it corresponds to a craniocaudal (CC) direction or a mediolateral oblique (MLO) direction. The x-ray source accordingly projects the x-ray radiation from different defined acquisition angles through the examination object onto the detector, which captures the projection images of the breast as raw datasets. Alternatively, however, both the detector and the x-ray source can be rotated around the examination object and in this way record projection images as raw datasets from different acquisition angles.

According to the invention, the raw data is—preferably only—recorded from lateral acquisition angles, i.e. the projection is performed obliquely to the central axis. In contrast to a conventional tomosynthesis scan, therefore, the acquisition angles in a range around the central axis are omitted and no central projection images are generated. This is because the examination instrument, that is to say e.g. a biopsy device, is preferably arranged, in particular with a vacuum-assisted biopsy needle, in the vicinity of the central axis. In the case of the central projection images, this would cause artifacts during the reconstruction, which makes the imaging or reconstruction more difficult. By means of the inventive use of the lateral acquisition angles for the acquisition of the raw data, it is possible to avoid these interference effects to a large extent. At the same time the patient's exposure to radiation is advantageously reduced as a result.

In such a procedure, the individual projection images are preferably acquired using a radiation dose which is so small that advantageously roughly only the radiation dose of a conventional mammogram is used for the entire acquisition. The result is that the contrast on the individual projection images is not sufficient to be able to discriminate details of the examination object, in particular of the region of interest. According to the invention, synthetic projections are first calculated from the raw data for this reason.

The synthetic projections can be generated from the raw data for example in that initially a volume dataset is reconstructed by means of known methods such as, e.g., filtered backprojection. Subsequently, in the course of a forward projection, the volume dataset is projected onto a virtual detector, as a result of which a virtual or synthetic projection is obtained. Preferably, however, no complete reconstruction of a volume dataset is undertaken, but rather only individual thin slices, particularly preferably precisely one, are reconstructed, from which the virtual projections are obtained by means of forward projections. This process is described for example in published patent application US 2014/0294138 A1, the contents of which are herewith incorporated by reference in their entirety. Alternatively, the synthetic projections are reconstructed directly from the raw data, as a result of which computing power can advantageously be saved compared with a complete volume reconstruction. This process is described for example in German patent DE 10 2011 087 337 B4, the contents of which are herewith incorporated by reference in their entirety.

In this case, the number of synthetic projections can be equal to the number of projection images acquired as raw data, though it may also be different, depending on requirements and the type of reconstruction, in other words may comprise more or fewer projection images.

The synthetic projections can be output for example into a memory of a computing unit (computer), via a network and/or on a display screen. In this case, the synthetic projections are preferably presented as a mammogram rotating through a limited range, which particularly preferably rotates substantially only in the same angular range as the acquisition angles. Compared to a slice image visualization of a conventional tomosynthesis scan, this enables a better spatial assignment as well as a higher degree of precision of the localization in the z-direction, i.e. perpendicularly to the image slices.

With the above and other objects in view there is also provided, in accordance with the invention, an image reconstruction device for visualizing a region of interest inside an examination object into which an examination instrument has been introduced, the device comprising:

an acquisition unit configured to acquire raw datasets from a plurality of lateral acquisition angles;

a calculation unit configured to calculate a plurality of synthetic projections from the raw datasets; and an output unit configured to output the synthetic projections in a form of an image sequence that represents the examination object in a rotating visualization.

In other words, the image reconstruction device mentioned above for visualizing a region of interest inside an examination object into which an examination instrument has been inserted comprises an acquisition unit, a calculation unit and an output unit. It is embodied in such a way that it performs the steps of a visualization method according to the invention.

With the above and other objects in view there is also provided, in accordance with the invention, a tomosynthesis system, comprising:

a tomosynthesis device having a source-detector arrangement configured for acquiring raw data of an examination object from a plurality of defined acquisition angles; and an image reconstruction device for visualizing a region of interest inside the examination object into which an examination instrument has been introduced, image reconstruction device including:

a calculation unit for calculating a plurality of synthetic projections from the raw datasets acquired by said tomosynthesis device; and  an output unit configured to output the synthetic projections in a form of an image sequence that represents the examination object in a rotating visualization.

In other words, the novel tomosynthesis system comprises a tomosynthesis device having a source-detector arrangement which is embodied for acquiring raw data of the examination object from defined acquisition angles, and also an image reconstruction device according to the invention.

Preferably, the tomosynthesis system also comprises a biopsy device having an examination instrument, i.e. having a biopsy needle, which is introduced into the examination object in the course of a biopsy, which is not encompassed within the scope of the invention, for the purpose of taking a tissue sample. During the biopsy, the method according to the invention can then be performed by means of the tomosynthesis system so that a maximally comprehensive, detailed and intuitive visualization is achieved for the purpose of monitoring and/or documenting the examination in order to facilitate a successful examination.

According to the information derived from the method according to the invention, the biopsy device can be correctively adjusted automatically or by operating staff, for example prior to the actual taking of a sample (which is not encompassed with the scope of the invention), which advantageously ensures a more accurate positioning during the intervention.

Most of the main components of the image reconstruction device according to the invention can be largely embodied in the form of software components. In principle, however, some of these components can also be realized in the form of software-assisted hardware, for example FPGAs (field-programmable gate arrays) or the like, in particular when there is a requirement for particularly fast calculations. Similarly, the required interfaces can be embodied as software interfaces, for example when it is simply a matter of importing data from other software components. They can, however, also be embodied as hardware-based interfaces which are controlled by suitable software.

In particular, the image reconstruction device according to the invention can be part of a user terminal of a tomosynthesis system.

A largely software-based implementation has the advantage that image reconstruction devices already used previously in the prior art can also be easily upgraded by means of a software update in order to operate in the manner according to the invention. To that extent, the object is also achieved by means of a corresponding computer program product having a computer program which can be loaded directly into a memory device of an image reconstruction device of a tomosynthesis system, and having program sections for the purpose of performing all steps of the method according to the invention when the program is executed in the image reconstruction device. As well as the computer program, such a computer program product may, where appropriate, also comprise additional constituent parts such as e.g. documentation and/or additional components, including hardware components, such as e.g. hardware keys (dongles, etc.) to allow use of the software.

A computer-readable medium, for example a memory stick, a hard disk or some other transportable or permanently installed data carrier, on which the program sections of the computer program that can be read in and executed by a computer unit of the image reconstruction device are stored, may be used for transporting the computer program to the image reconstruction device and/or for storing the same on or in the image reconstruction device. For this purpose, the computer unit may have e.g. one or more cooperating microprocessors or the like.

Further, particularly advantageous embodiments and developments of the invention will become apparent from the dependent claims as well as from the following description, wherein the independent claims of one claims category can also be developed analogously to the dependent claims or parts of the description of another claims category, and in particular also individual features of different exemplary embodiments or variants can be combined to create new exemplary embodiments or variants.

Since the central projection images in particular contribute to the generation of artifacts in the imaging session due to the arrangement of the examination instrument during the acquisition of the raw data, the raw datasets are preferably acquired at acquisition angles of at least 10°, particularly preferably at least 15°, to a central axis. In this case, as already mentioned hereinabove, the central axis extends in a direction of the patient's body, e.g. in a craniocaudal (CC) or mediolateral oblique (MLO) direction.

The raw datasets are preferably acquired at acquisition angles of at most 60°, particularly preferably at most 45°, quite particularly preferably at most 25°, to a central axis. By means of the synthetic projections that can be calculated from this raw data it is already possible to gain a good spatial impression of the region of interest.

Preferably, the number of lateral acquisition angles or the number of projection images acquired as raw data amounts to at least 10, particularly preferably 20. With 10 projection images, for example, 5 images per side are acquired in each case in relation to the central axis in an angular range of 15° to 25° to the central axis with angular distances of 2°. With 20 projection images, for example, 10 images per side are acquired in each case in relation to the central axis in an angular range of 15° to 25° to the central axis with angular distances of 1°. Using this number of projection images, it is already possible to generate synthetic projections with sufficient quality, and in this way the radiation exposure is advantageously kept at a low level for the patient.

In the method according to the invention, preferably two raw datasets are acquired in each case from acquisition angles which—referred to a central axis—are arranged opposite each other. The raw datasets are therefore preferably recorded or acquired with opposite ranges of the acquisition angles on both sides of the central axis. From the raw datasets, preferably two image sequences are determined which represent a rotating visualization of the region of interest from two different sides or from two different (central) directions. An even better spatial localization of the region of interest is made possible as a result.

The output of the synthetic projections preferably comprises a maximum intensity projection (MIP). Data representing a volume can be spatially visualized particularly intuitively by means of the maximum intensity projections. To that end, two-dimensional synthetic projections are calculated from the raw data that images the three-dimensional volume of the examination object by selecting in each case the data point or pixel having the maximum intensity during the reconstruction of the synthetic projections along a line of sight (projection direction of the synthetic projection).

In addition to the already described rotating visualization, the spatial perception of an operator can be improved even further if a slice dataset of the examination object is also provided. Preferably, therefore, a tomosynthesis scan has already been acquired before the examination instrument is introduced into the examination object. This advantageously avoids the examination instrument being the cause of artifacts during the acquisition of the tomosynthesis scan. The tomosynthesis scan is preferably output in addition to the image sequence so that the two datasets can be compared for the localization of the region of interest.

The raw data is preferably acquired before and/or after an actuation of the examination instrument. The raw data can therefore be acquired according to requirements before and, alternatively or in addition, also after the actuation of the examination instrument. The actuation of the examination instrument preferably entails the sample-taking process during the biopsy with the aid of a biopsy needle, referred to as the "fire". The raw data acquired prior to the actuation is accordingly referred to as "pre-fire" data, while the raw data acquired after the actuation is called "post-fire" data. Because the biopsy needle has already been inserted into the breast of the patient both before and after the fire, in a traditional imaging scan it would cause artifacts which make the visualization more difficult or in certain circumstances impossible. In contrast thereto, the method according to the invention enables a spatially good visualization of the position of the biopsy needle in relation to the region of interest, that is to say e.g. the microcalcification, to be achieved even under these conditions, thus allowing an improved tracking of the position of the biopsy needle or, as the case may be, a better documentation of the intervention. After the position of the biopsy needle has been checked, this can still be correctively adjusted e.g. by an operator, so that the intervention can be performed in a more targeted fashion.

Other features which are considered as characteristic for the invention are set forth in the appended claims.

Although the invention is illustrated and described herein as embodied in a visualizing of a region of interest, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

Like components are labeled with the same reference numerals in the various figures. The figures are generally not to scale.

DETAILED DESCRIPTION OF THE INVENTION

Figure 1:
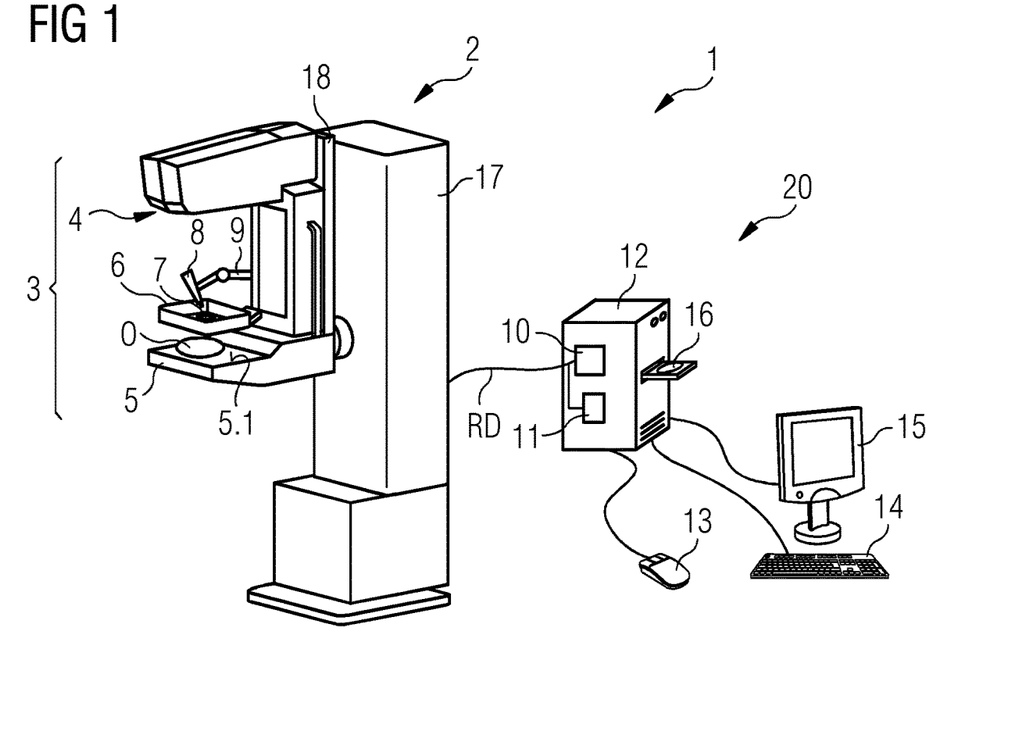
FIG. 1 shows a roughly schematic representation of an exemplary embodiment of a tomosynthesis system according to the invention.

Referring now to the figures of the drawing in detail and first, particularly, to FIG. 1 thereof, there is shown an exemplary embodiment of a tomosynthesis system 1 according to the invention in roughly schematic form. Relative direction indicators such as "up" and "down" etc. relate to a tomosynthesis system 1 that is set up for operation according to the proper specifications. The tomosynthesis system 1 comprises a tomosynthesis device 2 and a computer system 20. The tomosynthesis device 2 has a pedestal 17 and a source-detector arrangement 3, which in turn comprises an x-ray radiation source 4 (in the following also designated as x-ray source 4) and a detector 5 having a detection surface 5.1. During operation, the pedestal 17 stands upright on the base. The source-detector arrangement 3 is slidably connected to the pedestal 17 so that the height of the detector surface 5.1, i.e. its distance from the base, can be adjusted to a breast height of a patient.

A breast O of the patient (depicted schematically here) is positioned as the examination object O for an examination on the top side of the detector surface 5.1. Arranged above the breast O and the detector surface 5.1 is a paddle 6, which is slidably connected to the source-detector arrangement 3. For the examination, the breast O is compressed and at the same time fixed in position by lowering the paddle 6 down onto it so that a pressure is exerted onto the breast O between paddle 6 and detector surface 5.1. In its center, the paddle 6 has a circular cutout 7 through which the breast O is accessible for the examination.

The x-ray radiation source 4 is arranged and embodied opposite the detector 5 in such a way that the detector 5 captures x-ray radiation emitted by the source after at least some of the x-ray radiation has penetrated the breast O of the patient. Projections of the breast O are therefore acquired as raw data RD. In this arrangement, the x-ray radiation source 4 can be swiveled relative to the detector 5 by means of a rotary arm 18 through a range of, for example, ±25° about a home position, i.e. around a central axis MA, in which it is positioned vertically above the detection surface 5.1 (see also FIG. 3).

In addition, the tomosynthesis device 2 has a biopsy device 8 as examination instrument 8 and a robotic arm 9 as positioning device 9. The robotic arm 9 is fixedly connected at one end to the source-detector arrangement 3. The arm has articulated joints and motorized elements for positioning the biopsy device 8, which is connected to the free end of the arm. The biopsy device 8 comprises a needle holder and a biopsy needle (not depicted here) retained therein. The visualization method according to the invention is performed in order to visualize a biopsy, i.e. a removal of tissue for the purpose of a histological examination, by means of the tomosynthesis system 1, as described hereinbelow.

The computer system 20 comprises a computer unit 12 and, individually connected thereto, a mouse 13, a keyboard 14 and a screen 15. The screen 15 serves here as a display unit 15, while mouse 13 and keyboard 14 each serve as an input device. The computer unit 12 comprises an image reconstruction device 10 and a control device 11 (shown here schematically as blocks) and a drive 16 for reading CDs or DVDs. In this arrangement, the image reconstruction device 10 and the control device 11 can share components of the computer unit 12, such as e.g. memory, processors and the like. The computer system 20 can be arranged in the same room as the tomosynthesis device 2, or alternatively it can also be located in a neighboring control room or at an even further spatial distance.

Figure 2:
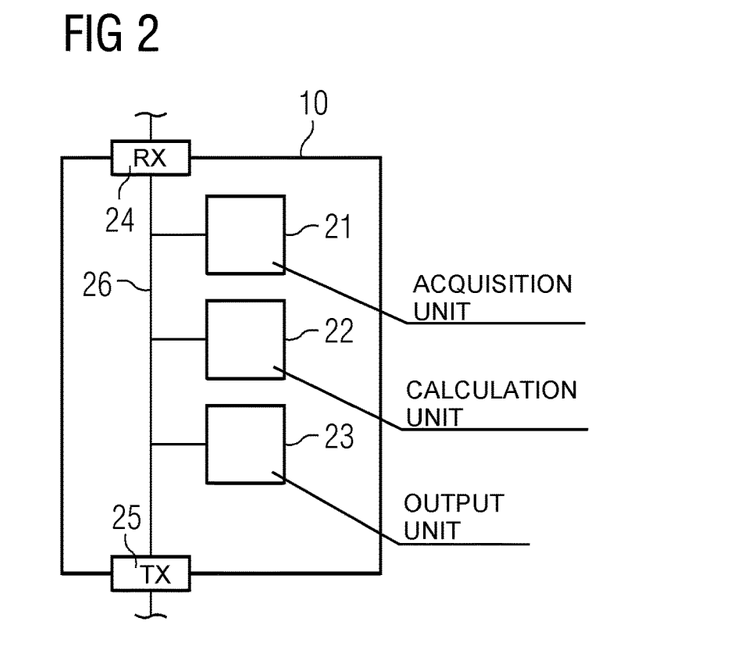
FIG. 2 shows a schematic block diagram of an exemplary embodiment of an image reconstruction device according to the invention.

FIG. 2 shows an exemplary embodiment of an image reconstruction device 10 according to the invention schematically in the form of a block diagram. The image reconstruction device 10 comprises an input data interface 24, an acquisition unit 21, a calculation unit 22, an output unit 23, and an output interface 25. The individual components of the image reconstruction device 10 are interconnected via a common bus 26, thus enabling data to be exchanged freely between the individual components according to requirements. The input data interface 24 can for example be connected via a network to further storage or memory devices or to a tomosynthesis device (see FIG. 1) and can receive data transmitted thereby. The output interface 25 can likewise be connected via a network to further storage or memory devices or else transfer the output data directly onto a screen, a projector, a touchscreen or the like. The cooperative interaction of the individual components of the control device is described below with reference to FIG. 4 and FIG. 5.

Figure 3:
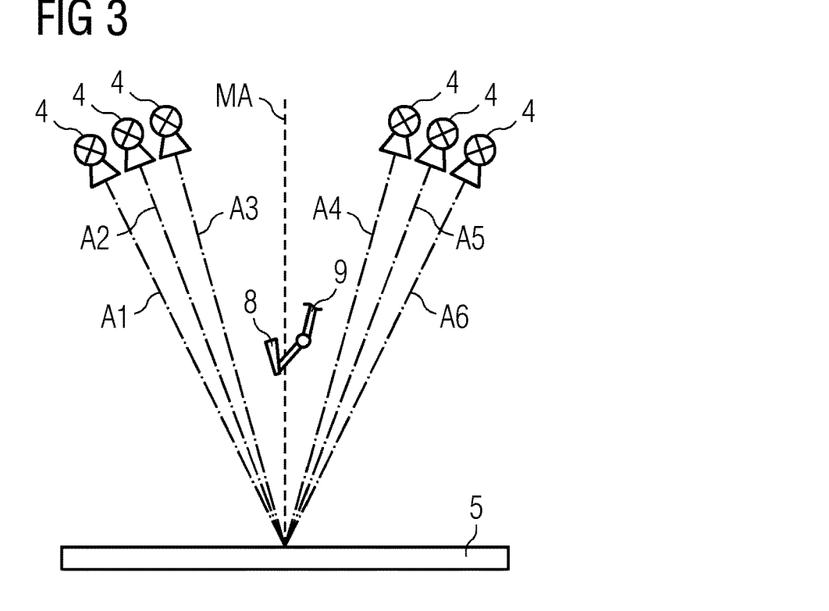
FIG. 3 shows a schematic representation of the arrangement of the ranges of the acquisition angles in an exemplary embodiment of a method according to the invention for visualizing a region of interest.

Referring to FIG. 3, an inventive lateral arrangement of the acquisition angles A1, A2, . . . , A6 is shown by way of example and in schematic form. For illustration purposes, the x-ray source 4 is depicted schematically in a number of positions, such that, depending on its position, a central x-ray beam emitted by it strikes the detector 5 at a defined acquisition angle A1, A2, . . . , A6. A central axis MA extends vertically on the detector. The biopsy device 8 and its robotic arm 9 (indicated on a small scale here) are arranged in the vicinity of the central axis MA. If the x-ray source were positioned in the vicinity of the central axis MA, the biopsy device 8 and the robotic arm 9 would block the beam path or lead to artifacts during the imaging. Consequently, no data is acquired in the vicinity of the central axis MA. Thus, according to the invention, only raw data RD acquired from the lateral acquisition angles A1, A2, . . . , A6 is recorded. The lateral acquisition angles A1, A2, . . . , A6 are arranged obliquely on both sides of the central axis MA and in this case are simultaneously positioned obliquely with respect to the detector 5. In this case, they assume angles of A3, A4=±15°; A2, A5=±20° and A1, A6=±25° to the central axis MA. Preferably, depending on requirements, raw data RD is additionally acquired or recorded at intermediate positions (not shown here).

Figure 4:
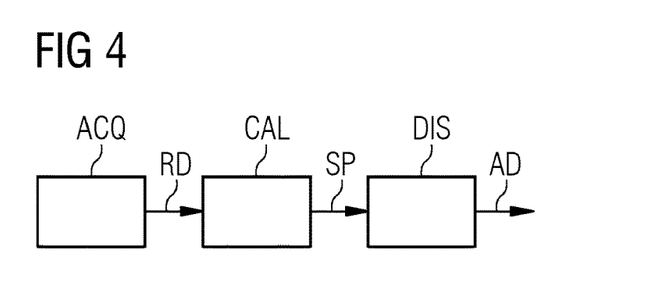
FIG. 4 shows a block diagram of an exemplary embodiment of a method according to the invention for visualizing a region of interest.

FIG. 4 shows by way of example a block diagram of a visualization method according to the invention. Raw data RD is acquired in a first step ACQ. To that end, the projection images detected at lateral acquisition angles A1, A2, . . . , A6 are received by the reconstruction unit 10 via the input interface 24 and forwarded over the bus 26 to the acquisition unit 21. In this case, the acquisition, which is not encompassed within the scope of the method according to the invention, can be completed immediately before the method, though it can also be performed spaced apart in time therefrom.

The projection images are produced at a low radiation dose, such that suitable synthetic projections SP are initially calculated from the raw data RD in a second step CAL for an assessment by an observer. This happens in the calculation unit 22 preferably by means of a direct reconstruction of the synthetic projections SP from the raw data RD, the result of which can be a maximum intensity projection or a rotating mammogram, according to requirements. No intermediate step in which a volume dataset is reconstructed as an auxiliary measure is therefore performed explicitly.

In a third step DIS, the synthetic projections SP are output by means of the output unit 23 via the output interface 25 as output data AD, which visualizes the examination object O as rotating in an image sequence. The individual calculated synthetic projections SP are therefore merged to form an image sequence AD, which is ordered in such a way that when the image sequence AD is run or played back, the impression is created in an observer that the visualized examination object O is rotating. When an output DIS is displayed on a screen 15, the observer can speed up, slow down or pause the running of the image sequence AD at any time with the aid of an input means such as e.g. the mouse 13 or the keyboard 14. Alternatively, the image sequence AD can also be output for example into a memory of the computer unit 12 or via a network.

Figure 5:
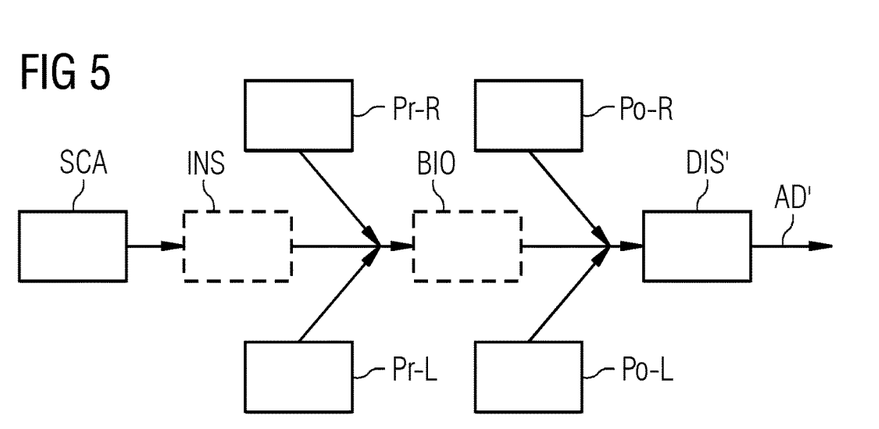
FIG. 5 shows a block diagram of a further exemplary embodiment of a method according to the invention for visualizing a region of interest.

FIG. 5 shows a block diagram of a further exemplary embodiment of a method according to the invention for visualizing a region of interest. Firstly, in a step SCA, a complete tomosynthesis scan is generated by means of a known method. This is used for planning the following intervention, i.e. preferably for target planning and particularly preferably also for path planning for a following biopsy with the aid of a biopsy device 8 having a biopsy needle. According to said planning, the biopsy needle is inserted into the examination object O in a following step INS (represented by a dashed outline), which is not encompassed within the scope of the method according to the invention.

Next, in order to maintain a visual check on the position of the biopsy needle, the method already described with reference to FIG. 4 is performed twice. For this purpose, in a step Pr-R, the region of interest is visualized from an angular range on the right side, and in a step Pr-L it is visualized from an angular range on the left side. The output data AD obtained from this (pre-fire data) can on the one hand, as depicted here, be buffered for a total output at the end of the method. On the other hand, it can also additionally be output simultaneously, e.g. on a screen 15, to allow an immediate check on the successful insertion INS of the biopsy needle so that, if necessary, a corrective adjustment of the position of the needle can be carried out. For this purpose, the pre-fire data can also be presented in combination with slide images obtained from the tomosynthesis scan in order to impart an even better spatial impression to the observer.

In a following step BIO (represented by a dashed outline), which is not encompassed within the scope of the method according to the invention, the sample taking BIO from the region of interest is accomplished by means of the biopsy needle.

Next, the inventive method described with reference to FIG. 4 is again performed twice. For this purpose, in a step Po-R, the region of interest is visualized from an angular range on the right side, and in a step Po-L it is visualized from an angular range on the left side. The output data AD obtained from this (post-fire data) can be output as already described with reference to the pre-fire data. In this way the success of the sample taking BIO can be checked on the one hand, and on the other hand the data can be buffered for the total output DIS' described below.

In a further step DIS', the total output DIS' of the total output data AD' takes place. In this case, the total output data AD' represents a documentation of the intervention as a whole. Comprised therein is the data of the tomosynthesis scan SCA, which is stored in the form of a slice image stack, the right-side pre-fire data, the left-side pre-fire data, as well as the right-side post-fire data and the left-side post-fire data. As a result of the compilation of all this data, a maximally comprehensive impression of the entire intervention can be conveyed to the observer.

In this scenario, the different views cooperatively interact to the effect that the advantages in the spatial perception of the individual datasets, i.e. of the slice data and the rotating visualization of the image sequences, synergistically complement one another. As a result, the region of interest and, where applicable, also the position of the biopsy needle can be localized and assessed more effectively than would be possible with just one of the datasets. According to the invention, the artifacts caused by the biopsy needle are simultaneously avoided during the imaging.

In conclusion, it is pointed out once again that the devices and methods described in detail in the foregoing are merely exemplary embodiments which can be modified in a wide variety of ways by the person skilled in the art without leaving the scope of protection of the invention. Furthermore, the use of the indefinite articles "a" or "an" does not exclude the possibility that the features in question may also be present more than once. Equally, the terms "device", "unit" and "system" do not rule out the possibility that the component in question consists of a plurality of cooperating subcomponents, which, where necessary, may also be spatially distributed.

The following is a summary list of reference numerals and the corresponding structure used in the above description of the invention:

1 Tomosynthesis system
2 Tomosynthesis device
3 Source-detector arrangement
4 X-ray radiation source
5 Detector
5.1 Detection surface
6 Paddle
7 Circular cutout
8 Examination instrument, biopsy device
9 Robotic arm
10 Image reconstruction device
11 Control device
12 Computer unit
13 Mouse
14 Keyboard
15 Screen
16 Drive
17 Pedestal
18 Rotary arm
20 Computer system
21 Acquisition unit
22 Calculation unit
23 Output unit
24 Input data interface
25 Output interface
26 Bus
A1, A2, . . . , A6 Acquisition angles
SP Synthetic projections
AD Output data
AD' Total output data
MA Central axis
O Examination object, breast
RD Raw data
ACQ, CAL, DIS Method steps
BIO, DIS', INS, Po-L, Po-R, Pr-L, Pr-R Method steps

The invention claimed is:

1. A method of visualizing a region of interest inside an examination object, the examination object having an examination instrument inserted therein, the method comprising:
providing a tomosynthesis system and performing the following steps with the tomosynthesis system;
acquiring raw datasets from a plurality of lateral acquisition angles oblique to a central axis, including from an angular range on a right side of the central axis and from an angular range on a left side of the central axis, while omitting acquisition angles in a range around the central axis in a vicinity of the examination instrument;
calculating a plurality of synthetic projections from the raw datasets; and
outputting the synthetic projections in an image sequence that represents the examination object in a rotating visualization.

2. The method according to claim 1, which comprises acquiring the raw datasets at acquisition angles of at least 10° relative to the central axis.

3. The method according to claim 2, which comprises acquiring the raw datasets at acquisition angles of at least 15° relative to the central axis.

4. The method according to claim 1, which comprises acquiring the raw datasets at acquisition angles of no more than 60° relative to the central axis.

5. The method according to claim 4, which comprises acquiring the raw datasets at acquisition angles of no more than 45° relative to the central axis.

6. The method according to claim 1, which comprises acquiring the raw datasets at acquisition angles of no more than 25° relative to the central axis.

7. The method according to claim 1, which comprises acquiring the raw datasets at acquisition angles within a range from 10° to 60° relative to the central axis.

8. The method according to claim 1, which comprises acquiring the raw datasets with at least 10 lateral acquisition angles.

9. The method according to claim 8, which comprises acquiring the raw datasets with at least 20 lateral acquisition angles.

10. The method according to claim 1, which comprises acquiring two raw datasets in each case from acquisition angles which, referred to the central axis, are arranged opposite each other.

11. The method according to claim 1, wherein an output of the synthetic projections comprises a maximum intensity projection.

12. The method according to claim 1, which comprises acquiring a tomosynthesis scan before the examination instrument is introduced into the examination object.

13. The method according to claim 12, which comprises outputting the tomosynthesis scan in addition to the image sequence.

14. The method according to claim 1, which comprises actuating the examination instrument and acquiring the raw data before and/or after an actuation of the examination instrument.

15. A computer program product, comprising a non-transistory computer program to be loaded directly into a memory of an image reconstruction device of a tomosynthesis system, and having program code for causing the reconstruction device to carry out the method according to claim 1 when the computer program is executed in the image reconstruction device of the tomosynthesis system.

16. A computer-readable medium storing thereon program sections to be read into and executed by a computer unit to cause the computer unit to perform all steps of the method according to claim 1 when the program sections are executed by the computer unit.

17. An image reconstruction device for visualizing a region of interest inside an examination object into which an examination instrument has been introduced, the device comprising:
an acquisition unit configured to acquire raw datasets from a plurality of lateral acquisition angles oblique to a central axis, including from an angular range on a right side of the central axis and from an angular range on a left side of the central axis, while omitting acquisition angles in a range around the central axis in a vicinity of the examination instrument;
a calculation unit configured to calculate a plurality of synthetic projections from the raw datasets; and an output unit configured to output the synthetic projections in a form of an image sequence that represents the examination object in a rotating visualization.

18. A tomosynthesis system, comprising:

a tomosynthesis device having a source-detector arrangement configured for acquiring raw data of an examination object from a plurality of defined acquisition angles oblique to a central axis, including from an angular range on a right side of the central axis and from an angular range on a left side of the central axis, while omitting acquisition angles in a range around the central axis in a vicinity of an examination instrument introduced into the examination object; and an image reconstruction device for visualizing a region of interest inside the examination object into which the examination instrument has been introduced, image reconstruction device including:

a calculation unit for calculating a plurality of synthetic projections from the raw datasets acquired by said tomosynthesis device; and an output unit configured to output the synthetic projections in a form of an image sequence that represents the examination object in a rotating visualization.

* * * * *